United States Patent
Chen (10) Patent No.: US 11,047,932 B2
(45) Date of Patent: Jun. 29, 2021

(54) DETERMINING COMPOSITION OF METAL ARTIFACTS USING DYNAMIC ELECTROMAGNETIC PROFILE MEASUREMENTS

(71) Applicant: Lucas Chen, Pasadena, CA (US)

(72) Inventor: Lucas Chen, Pasadena, CA (US)

(*) Notice: Subject to any disclaimer, the term of this patent is extended or adjusted under 35 U.S.C. 154(b) by 0 days.

(21) Appl. No.: 16/819,009

(22) Filed: Mar. 13, 2020

(65) Prior Publication Data
US 2020/0217905 A1  Jul. 9, 2020

(51) Int. Cl.
*G01R 33/02* (2006.01)
*G01R 33/00* (2006.01)

(52) U.S. Cl.
CPC ......... *G01R 33/02* (2013.01); *G01R 33/0094* (2013.01)

(58) Field of Classification Search
CPC ..... G01N 33/2028; G01N 27/72; G01R 33/12
See application file for complete search history.

(56) References Cited

U.S. PATENT DOCUMENTS

| | | | | |
|---|---|---|---|---|
| 6,586,938 | B1* | 7/2003 | Paltoglou | G01V 3/104 324/329 |
| 2002/0075001 | A1* | 6/2002 | Goodman | G01V 3/15 324/326 |
| 2013/0307532 | A1* | 11/2013 | Reime | G01V 3/107 324/239 |
| 2014/0225606 | A1* | 8/2014 | Endo | G01R 33/0322 324/260 |
| 2016/0178537 | A1* | 6/2016 | Leek | G01V 3/38 324/637 |
| 2017/0307566 | A1* | 10/2017 | Ishikawa | G01N 27/72 |

* cited by examiner

*Primary Examiner* — Alvaro E Fortich
(74) *Attorney, Agent, or Firm* — McDermott Will & Emery LLP

(57) ABSTRACT

An apparatus determines the composition of a metal artifact. The apparatus includes an electrical current source, a metal artifact to be tested, two electrical cables, and a first electrical cable and a second electrical cable different from the first electrical cable. Each of the first electrical cable and the second electrical cable is connected between the electrical current source and the metal artifact. During a test, the electrical current source outputs current. When the electrical current source outputs the current, the current travel through at least a portion of the metal artifact. The apparatus further includes a magnetic field sensor that detects, during the test, a magnetic field generated by the metal artifact when the current travels through the at least the portion of the metal artifact. The magnetic field sensor is disposed within a predetermined distance of the metal artifact during the test.

14 Claims, 3 Drawing Sheets

DETERMINING COMPOSITION OF METAL ARTIFACTS USING DYNAMIC ELECTROMAGNETIC PROFILE MEASUREMENTS

BACKGROUND

Technical Field

This disclosure relates to metal artifacts, magnetic fields, and metal composition of the metal artifacts.

Description of Related Art

Development of metallurgy is a hallmark of civilization and has been an integral part of human history. The utilization of metals is generally known to have started as early as 9000 BC when native copper was hammered into awls, pins, and other small metal objects. The discovery of pyrometallurgy in 5000 BC allowed the extraction of metals from ores at a larger quantity and higher purity.

During the Bronze Age, which began around 3500 BC, humans developed bronze—an alloy of tin and copper that is stronger, more resistant to corrosion, and more malleable than the existing metals at that time. The Bronze Age was a global development in which societies and civilizations mastered the technology of producing their own unique styles of bronze vessels. Today, these bronze artifacts are treasured due to their durability, as well as their ability to retain original imprinted designs due to their structural integrity.

SUMMARY

According to certain aspects of the present disclosure, an apparatus for determining composition of a metal artifact is provided. The apparatus includes an electrical current source, a metal artifact to be tested, and a first electrical cable and a second electrical cable different from the first electrical cable. Each cable is connected between the electrical current source and the metal artifact. During a test, the electrical current source outputs current. When the electrical current source outputs the current, the current travels through at least a portion of the metal artifact. The apparatus further includes a magnetic field sensor that detects, during the test, a magnetic field generated by the metal artifact when the current travels through at least a portion of the metal artifact. The magnetic field sensor is disposed within a predetermined distance of the metal artifact during the test.

According to certain aspects of the present disclosure, a method for determining composition of a metal artifact is provided. The method includes electrically connecting an electrical current source to the metal artifact so as to cause current from the electrical current source to travel through at least a portion of the metal artifact. The method also includes placing a magnetic field sensor within a predetermined distance of the metal artifact. The method further includes activating the electrical current source to generate and output current so that the current travels through at least a portion of the metal artifact. The method also includes measuring, using the magnetic field sensor, the magnetic field generated by the metal artifact while current travels through the at least a portion of the metal artifact. The method includes determining composition of the metal artifact based on the measured magnetic field.

It is understood that other configurations of the subject technology will become readily apparent to those skilled in the art from the following detailed description, wherein various configurations of the subject technology are shown and described by way of illustration. As will be realized, the subject technology is capable of other and different configurations and its several details are capable of modification in various other respects, all without departing from the scope of the subject technology. Accordingly, the drawings and detailed description are to be regarded as illustrative in nature and not as restrictive.

BRIEF DESCRIPTION OF DRAWINGS

The drawings are of illustrative embodiments. They do not illustrate all embodiments. Other embodiments may be used in addition or instead. Details that may be apparent or unnecessary may be omitted to save space or for more effective illustration. Some embodiments may be practiced with additional components or steps and/or without all of the components or steps that are illustrated. When the same numeral appears in different drawings, it refers to the same or like components or steps.

In one or more implementations, not all of the depicted components in each figure may be required, and one or more implementations may include additional components not shown in a figure. Variations in the arrangement and type of the components may be made without departing from the scope of the subject disclosure. Additional components, different components, or fewer components may be utilized within the scope of the subject disclosure.

In addition, each of the drawings is a schematic diagram and thus is not necessarily strictly illustrated. In each of the drawings, substantially the same structural components are assigned with the same reference signs, and redundant descriptions will be omitted or simplified.

DETAILED DESCRIPTION OF ILLUSTRATIVE EMBODIMENTS

The detailed description set forth below is intended as a description of various implementations and is not intended to represent the only implementations in which the subject technology may be practiced. As those skilled in the art would realize, the described implementations may be modified in various different ways, all without departing from the scope of the present disclosure. For example, while the barricade systems discussed herein may be implemented in many different forms, the disclosure will show in the drawings, and will herein describe in detail, implementations with the understanding that the present description is to be considered as an exemplification of the principles of the selectively-configurable barricade system and is not intended to limit the broad aspects of the disclosure to the implementations illustrated. Accordingly, the drawings and description are to be regarded as illustrative in nature and not restrictive.

Metal artifacts produced during the Bronze Age were handcrafted using non-standardized alloy content and conditions. The alloy content and conditions varied by regions and civilizations, and further varied by individuals as those metal artifacts were handcrafted. As each piece was handcrafted of non-standardized alloy content and conditions, the identification and classification of metal artifacts, such as these bronze vessels, are often difficult.

Over the years, different noninvasive tests have been developed. For example, a streak test method can assess metal hardness by scratching the surfaces of metal artifacts. However, this method is unreliable in identifying metal content. As another example of the conventional method, energy spectrometry projects an X-ray beam to a metal artifact's surface, and the emitted secondary x-ray signal, which can provide characteristics of the metal, is examined. However, this method can only detect the metal on the surface of the metal artifact and is not usable if the metal artifact is painted or plated with a different metal.

Some invasive methods have also been utilized. For example, a spot analysis dissolves a small piece of metal from a metal artifact in a chemical mix to determine metal composition of the metal artifact. However, the spot analysis method is destructive as the small piece of metal is scraped off of the metal artifact, and the spot analysis method can only sample a small portion of the metal artifact. Another example of the invasive method is a neutron activation analysis in which a metal sample from a metal artifact is placed in a nuclear reactor, and the emitted gamma ray from bombarding neutron beams is examined. This neutron activation analysis, however, is expensive and also destructive, and can only analyze a small sample of the metal artifact.

Moreover, because it has been shown that copper and tin often do not mix uniformly as copper and tin have different melting points, bronze artifacts have different metal compositions within their structures. Consequently, taking a small sample of the bronze for atomic or chemical analysis may provide misleading information. Taking larger or more samples, while providing more data, would severely damage or destroy the valuable artifact.

In addition to being inaccurate and destructive, the conventional methods of metal composition identification may require expensive laboratories. As these methods can require expensive and cumbersome equipment, these methods are not readily available nor practical for archaeologists examining an uncovered metal artifacts, such as bronze vessel, at a dig site. A system and method for determining the metal composition of metal artifacts that are mobile, economical, and compact is therefore needed.

To address the need, the disclosed technique provides for more accurate identification of the metal composition of the metal artifacts without destructing the metal artifacts using dynamic electromagnetic profile of the metal artifact at different levels of electric current.

As noted above, metal artifacts, such as bronzeware, from each region and civilization are composed of different levels of copper and tin since the local metal ores are different. This may be because, before the creation of the periodic table, one had little to no understanding of chemistry and chemical composition. For example, since copper and tin have different electrical conductivity (with tin only having 15% of copper's electrical conductivity), bronzeware of different copper-tin ratios has different electrical conductivities, thus different dynamic electromagnetic profiles. In addition, as much ancient bronzeware invariably contains various combinations of arsenic, lead, phosphorus, aluminum, manganese and silicon from local ores, and bronze made in different parts of the world have very different magnetic profiles. Thus, scanning different regions of the metal artifact so to scan across the entire metal artifact and detecting the dynamic magnetic profile at different levels of electric current at each region of the metal artifact allow to detect the different compositions at each region. This compiles a magnetic map of the metal artifact generating a unique magnetic signature for the metal artifact.

Because this technique identifies the metal composition of bronzeware, vessels, coins, statues, or antiques, without cumbersome equipment, this technique can be used at an archaeological site to rapidly identify uncovered bronzeware, or at an art auction to verify the history and region of bronzeware. It can also be used to construct a magnetic signature that is unique for each piece of bronzeware and provides an identification profile of the bronzeware for insurance purposes.

Figure 1:
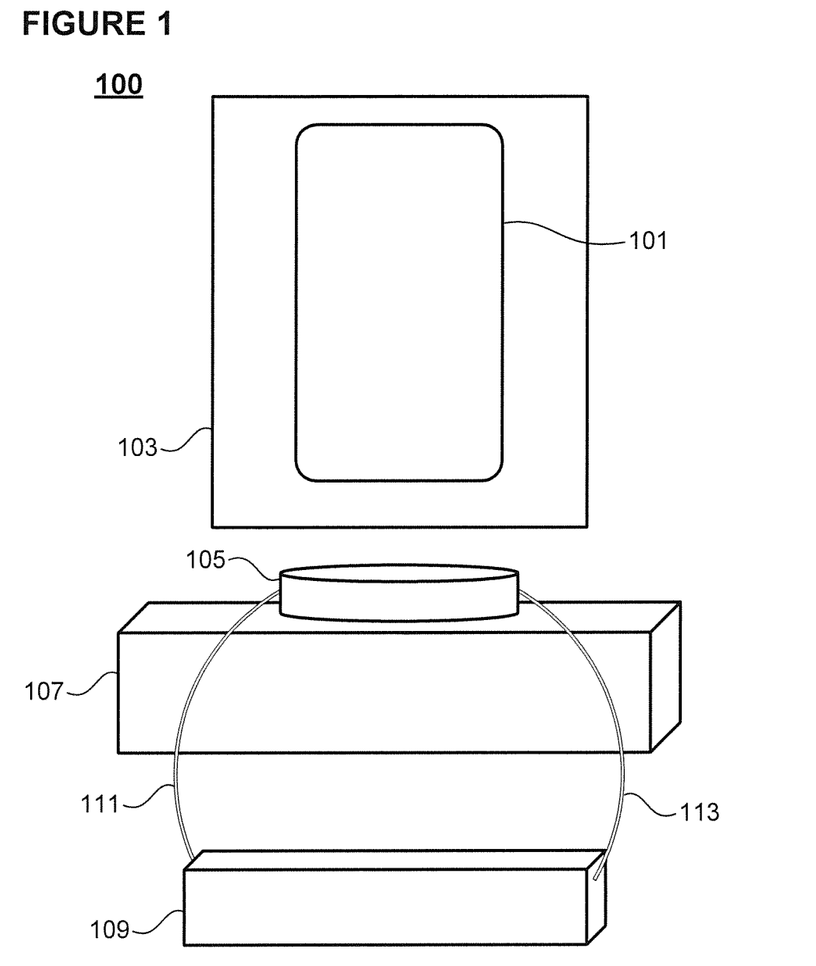
FIG. 1 illustrates an example of an apparatus for determining the composition of metal artifacts according to certain aspects of the disclosure.

FIG. 1 illustrates an example of an apparatus 100 for determining the composition of metal artifacts according to certain aspects of the disclosure. The apparatus 100 may include a magnetic field sensor 101, a sensor holder 103, a metal artifact 105, a metal artifact holder 107, an electrical current source 109, a first electrical cable 111, and a second electrical cable 113. The magnetic field sensor 101 is securely held in position by the sensor holder 103. The metal artifact 105 is securely held in position by the metal artifact holder 107. The electrical current source 109 is connected to the metal artifact 105 by the first and second electrical cables 111 and 113.

The magnetic field sensor 101 may be capable of measuring the magnitude and/or direction of a magnetic field in which the sensor is present. The magnetic field sensor 101 may include a magnetometer. Magnetometers may be part of mobile devices, such as an smartphones and tablets. The magnetometer in a mobile device may be in form of an application installed in the mobile device. For example, the magnetometer applications may be the Magnetscape v. 1.1 (available from Toon, iic), EMF Detector (available from Appreciate Studios), and Tesla Recorder (available from Exelerus). The magnetometer applications, when launched, accesses the magnetometer and displays, on a display of the mobile device, magnetic field information sensed by the magnetometer.

Figure 2:
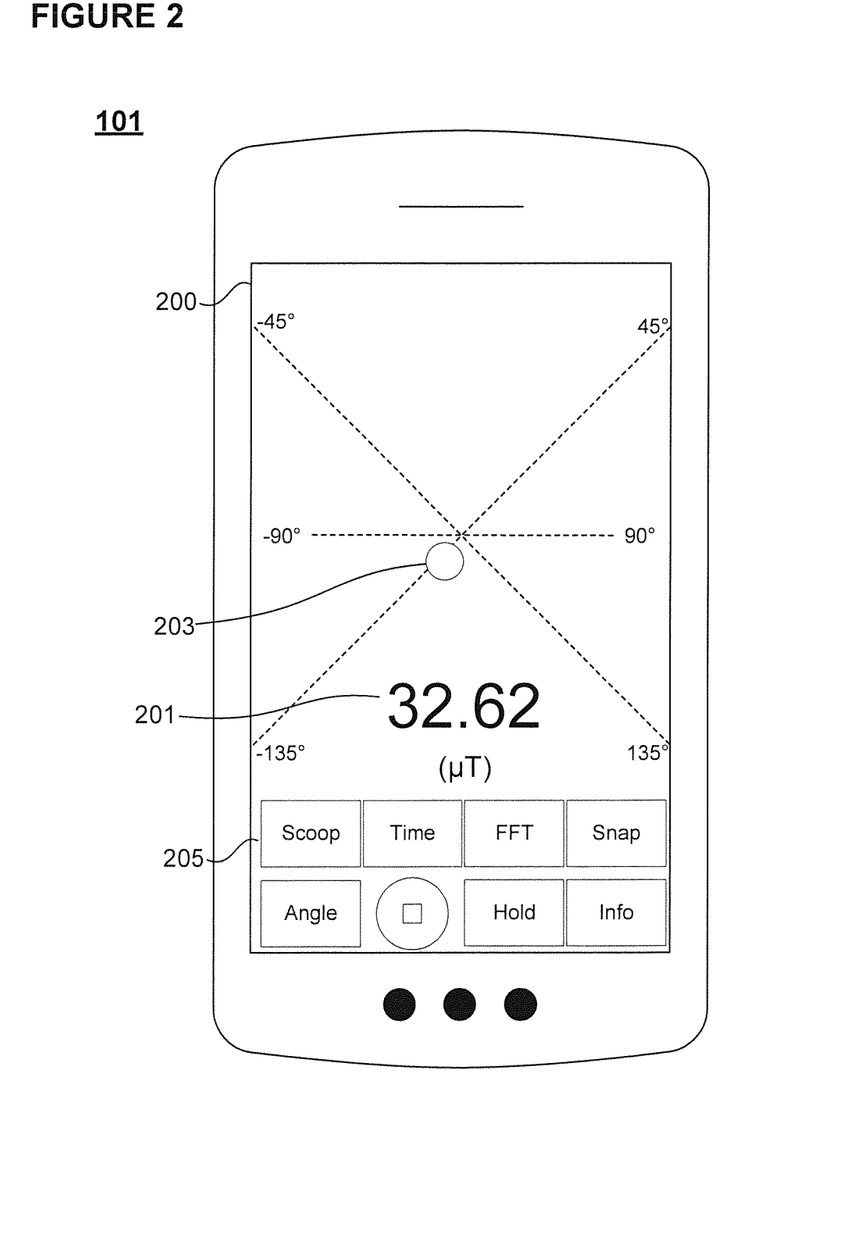
FIG. 2 illustrates an example of magnetic field measurements displayed on a mobile device according to certain aspects of the disclosure.

FIG. 2 illustrates an example of magnetic field measurements displayed on a display 200 of the mobile device 101. The magnetic field measurements depicted in FIG. 2 resemble the measurements being made by a magnetometer in a mobile device using the Magnetscape Application. As illustrated in FIG. 2, the display 200 may include magnitude information 201 that indicates the magnitude of the magnetic field surrounding the magnetometer, and the position of a pointer 203 indicates the vector direction of this magnetic North Pole or other reference as directional information. The display 200 further includes a group of functional keys for maneuvering the magnetometer application. The number of keys may not be limited to eight as shown in FIG. 2, but may be less or more than the numbers of the keys shown in FIG. 2. The dimensions of these elements are exemplary only, and other sizes and shapes are possible.

Returning to FIG. 1, the sensor holder 103 may be made of nonferrous material, such as rubber or plastic, so as not to interfere with the current during the test of the metal artifact 105. The sensor holder 103 may have a configuration that allows the magnetic field sensor 101 to be attached to (e.g., by a snapping or strapping action) and detached from (e.g., by an un-snapping or un-strapping action) the sensor holder 103. The sensor holder 103 may hold the magnetic field sensor 101 in a secure position when attached to the sensor holder 103. Examples of sensor holders include mobile phone holders, hand soldering stands, grip wall mount holders, web clamps that hold delicate materials, jaw clamps, and other holding devices that include flat surfaces and are made of electrical insulating materials.

The metal artifact 105 may be made of bronze materials. The metal artifact 105 may include bronze vessels, bronze bells, bronze statues, bronze weapons, bronze coins, and the like. The metal artifact 105 may not be limited to historical metal objects, and may be any metal objects that are valuable to their owners who do not wish to leave sight of the object and do not wish to have any part of the object destructed.

The metal artifact holder 107 may be made of nonferrous material, such as rubber or plastic. The metal artifact holder 103 may have a configuration that allows the metal artifact 105 to be attached to (e.g., by a snapping or strapping action) and detached from (e.g., by an un-snapping or un-strapping action) the metal artifact holder 107. The metal artifact holder 107 may hold the metal artifact 105 in a secure position when attached to the blade holder 107. Examples of metal artifact holders include hand soldering stands, grip wall mount holders, web clamps that hold delicate materials, jaw clamps, and other holding devices that include flat surfaces for placing the metal artifact 105 and are made of electrical insulating materials.

The electrical current source 109 may include one or more batteries, photocells, or electronic power supplies, such as a rechargeable lead acid battery, a high capacity rechargeable battery, and a lantern battery. The electrical current source 109 may be configured to deliver a DC or AC current at a predetermined or user-specified level, or at one of several user-selected levels of current.

The first and second electrical cables 111 and 113 may be configured to conduct electricity and may be copper or aluminum wires or other types of elongated lengths of electrically conductive metal. Each of the first and second electrical cables 111 and 113 may be connected at one of their ends to the electrical current source 109. The other ends of the first and second electrical cables 111 and 113 may be detachably connected to the metal artifact 105 at different locations on the metal artifact 105. The other ends of the first and second electrical cables 111 and 113 may include alligator clips to be securely connected to the metal artifact 105 during the test and easily detached from the metal artifact 105 after the test.

In some embodiments, the first electrical cable 111 may be detachably attached at a first position of the metal artifact 105, and the second electrical cable 113 may be detachably connected to a second position of the metal artifact 105, where the second position of the metal artifact 105 is different from the first position of the metal artifact 105.

Figure 3:
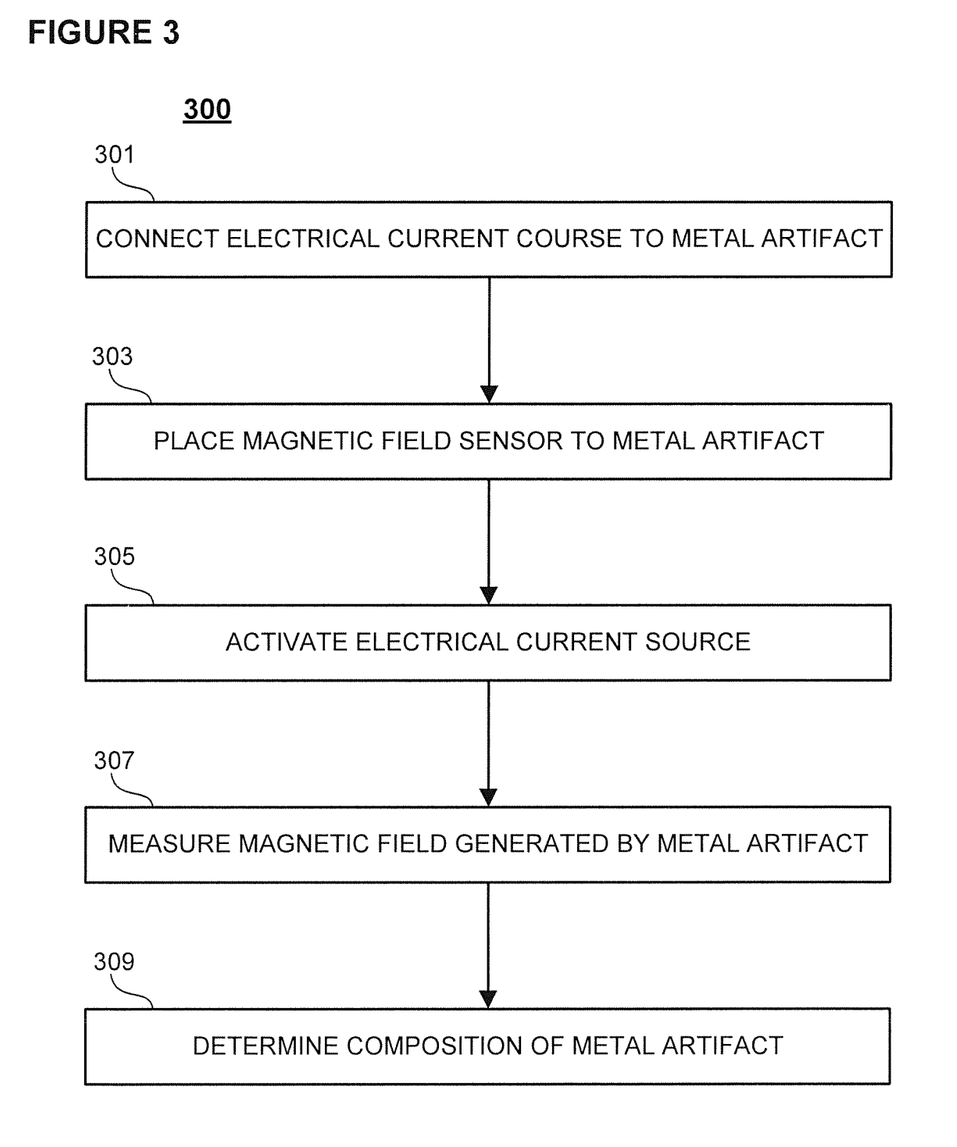
FIG. 3 illustrates an example of a process for determining the composition of metal artifacts according to certain aspects of the disclosure.

FIG. 3 illustrates a flowchart illustrating an example of a process 300 for determining the metal composition of the metal artifact 105 according to example aspects of the subject technology. For explanatory purposes, the various blocks of example process 300 are described herein with reference to the components and/or processes described herein. Further, for explanatory purposes, the blocks of example process 300 are described as occurring in serial, or linearly. However, multiple blocks of example process 300 may occur in parallel. In addition, the blocks of example process 300 need not be performed in the order shown and/or one or more of the blocks of example process 300 need not be performed.

At block 301, the electrical current source 109 may be detachably connected to the metal artifact 105 using the first and second electrical cables 111 and 113 and, when present, the alligator clips at each of the ends of the electrical cables 111 and 113. For example, the first electrical cable 111 may be detachably attached at a first location of the metal artifact 105, and the second electrical cable 113 may be detachably connected to second location on the metal artifact 105, where the first location and the second location differ from each other. The separation distance between the first location and the second location on the metal artifact to which the electrical cables 111 and 113 attach may vary. For example, the first location and the second location may be separated by 0.5 inches or by another amount.

At block 303, the magnetic field sensor 101 is placed within a predetermined distance of the metal artifact 105. The predetermined distance may be, for example, 0-3 inches. The position of the metal artifact 105 with respect to the magnetic field sensor 101 may be adjusted so as to cause the magnetic field sensor 101 to be located in very close proximity (e.g., 0-3 inches away) to the metal artifact 105 and approximately at the midpoint between where the electrical cables 111 and 113 will connect to the metal artifact 105.

During the test, the magnetic field sensor 101 may be firmly attached to the sensor holder 103 so as to ensure that it does not accidentally move during the testing process. In some embodiments, a sensor holder 103 may not be used, and steadily held by a user.

Prior to the test, the rotational position of the sensor holder 103 may be adjusted until the directional information 203 indicates a desired reference direction, such as 0°. In some embodiments, a sensor holder 103 may not be used, in which case the rotational position of the magnetic field sensor 101 may be adjusted directly. In some embodiments of this process, adjustment of the rotational position of the sensor holder 103 and/or the magnetic field sensor 101 itself may be omitted.

Also prior to the test, the measurements of the static magnetic field (i.e., caused by gravity) may be made by the magnetic field sensor 101, such as its magnitude information 201 and directional information 203, and recorded. This measurement may be made without the metal artifact 105 being in the metal artifact holder 107 or otherwise in proximity to the magnetic field sensor 101. (A magnetic field that does not include flux caused by current running through the metal artifact 105 is sometimes referred to herein as a static magnetic field, while a magnetic field that does include flux cause by current running through the metal artifact 105 is sometimes referred to herein as a dynamic magnetic field). In some embodiments of this process, this step measurement may be omitted.

During the test, the metal artifact 105 may be placed in the metal artifact holder 107 in a fixed position. In some embodiments, the metal artifact holder 107 may be omitted, in which case this step may be omitted.

Prior to the test, the angular position of the metal artifact 105 may be adjusted relative to the North Pole and/or the angular position of the magnetic field sensor 101. The location of the metal artifact 105 relative to the magnetic field sensor 101 may also be adjusted.

At block 305, the electrical current source 109 may be activated to cause an AC or DC current to flow through the portion of the metal artifact 105 that lies between the first location and the second location on the metal artifact to which the first and second electrical cables 111 and 113 are connected. During this step, a measurement of the dynamic magnetic field (caused by gravity and the current traveling through the metal artifact 105) may be made by the magnetic field sensor 101, such as its magnitude information 201 and directional information 203, and recorded.

At block 307, a measurement of the dynamic magnetic field (caused by gravity and the different level of current traveling through the metal artifact 105) may be made by the magnetic field sensor 101, such as its magnitude information 201 and directional information 203, and recorded. In some embodiments, the electrical current source 109 may be adjusted to cause a different level of AC or DC current to flow through the portion of the metal artifact 105 that lies between the first location and the second location on the metal artifact 105 to which the first and second electrical cables 111 and 113 are connected.

In some embodiments, the first and second electrical cables 111 and 113 may be detached from the first location and the second location on the metal artifact 105 and attached to a third location and a fourth location of the metal artifact 105. Block 307 may be repeated for the portion of the metal artifact 105 that lies between the third location and the fourth location on the metal artifact 105 to which the first and second electrical cables 111 and 113 are newly connected. Block 307 may be repeated until the entirety of the metal artifact 105 is measured.

At block 309, the quality of the metal artifact 105 may be determined based on one or more or all of the magnetic field measurements that were recorded during the process 300. IN some embodiments, an electromagnetic profile of the metal artifact 105 is generated based on one or more or all of the magnetic field measurements that were recorded. In some embodiments, a magnetic map of the metal artifact that indicates a unique magnetic signature specific to the metal artifact may be generated based on one or more or all of the magnetic field measurements that were recorded. The metal composition determination may also be based upon comparing the magnetic field measurements of the metal artifact that is being tested with comparable magnetic field measurements made of metal artifacts having the known metal compositions.

The components, steps, features, objects, benefits, and advantages that have been discussed are merely illustrative. None of them, nor the discussions relating to them, are intended to limit the scope of protection in any way. Numerous other embodiments are also contemplated. These include embodiments that have fewer, additional, and/or different components, steps, features, objects, benefits, and advantages. These also include embodiments in which the components and/or steps are arranged and/or ordered differently.

While some implementations have been illustrated and described, numerous modifications come to mind without significantly departing from the spirit of the disclosure, and the scope of protection is only limited by the scope of the accompanying claims. Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference. Furthermore, to the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments. Phrases such as an aspect, the aspect, another aspect, some aspects, one or more aspects, an implementation, the implementation, another implementation, some implementations, one or more implementations, an embodiment, the embodiment, another embodiment, some embodiments, one or more embodiments, a configuration, the configuration, another configuration, some configurations, one or more configurations, the subject technology, the disclosure, the present disclosure, other variations thereof and alike are for convenience and do not imply that a disclosure relating to such phrase(s) is essential to the subject technology or that such disclosure applies to all configurations of the subject technology. A disclosure relating to such phrase(s) may apply to all configurations, or one or more configurations. A disclosure relating to such phrase(s) may provide one or more examples. A phrase such as an aspect or some aspects may refer to one or more aspects and vice versa, and this applies similarly to other foregoing phrases.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Underlined and/or italicized headings and subheadings are used for convenience only, do not limit the subject technology, and are not referred to in connection with the interpretation of the description of the subject technology. Relational terms such as first and second and the like may be used to distinguish one entity or action from another without necessarily requiring or implying any actual such relationship or order between such entities or actions. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While this specification contains many specifics, these should not be construed as limitations on the scope of what may be claimed, but rather as descriptions of particular implementations of the subject matter. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

The subject matter of this specification has been described in terms of particular aspects, but other aspects can be implemented and are within the scope of the following claims. For example, while operations are depicted in the drawings in a particular order, this should not be understood as requiring that such operations be performed in the particular order shown or in sequential order, or that all illustrated operations be performed, to achieve desirable results. The actions recited in the claims can be performed in a different order and still achieve desirable results. As one example, the processes depicted in the accompanying figures do not necessarily require the particular order shown, or sequential order, to achieve desirable results. In certain circumstances, multitasking and parallel processing may be advantageous. Moreover, the separation of various system components in the aspects described above should not be understood as requiring such separation in all aspects, and it should be understood that the described program components and systems can generally be integrated together in a single product or packaged into multiple products.

The title, background, brief description of the drawings, abstract, and drawings are hereby incorporated into the disclosure and are provided as illustrative examples of the disclosure, not as restrictive descriptions. It is submitted with the understanding that they will not be used to limit the scope or meaning of the claims. In addition, in the detailed description, it can be seen that the description provides illustrative examples and the various features are grouped together in various implementations for the purpose of streamlining the disclosure. The method of disclosure is not to be interpreted as reflecting an intention that the claimed subject matter requires more features than are expressly recited in each claim. Rather, as the claims reflect, inventive subject matter lies in less than all features of a single disclosed configuration or operation. The claims are hereby incorporated into the detailed description, with each claim standing on its own as a separately claimed subject matter.

The claims are not intended to be limited to the aspects described herein, but are to be accorded the full scope consistent with the language claims and to encompass all legal equivalents. Notwithstanding, none of the claims are intended to embrace subject matter that fails to satisfy the requirements of the applicable patent law, nor should they be interpreted in such a way.

The disclosed systems and methods are well adapted to attain the ends and advantages mentioned as well as those that are inherent therein. The particular implementations disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative implementations disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

As used herein, the phrase "at least one of" preceding a series of items, with the terms "and" or "or" to separate any of the items, modifies the list as a whole, rather than each article of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

All articles, patents, patent applications, and other publications that have been cited in this disclosure are incorporated herein by reference.

The phrase "means for" when used in a claim is intended to and should be interpreted to embrace the corresponding structures and materials that have been described and their equivalents. Similarly, the phrase "step for" when used in a claim is intended to and should be interpreted to embrace the corresponding acts that have been described and their equivalents. The absence of these phrases from a claim means that the claim is not intended to and should not be interpreted to be limited to these corresponding structures, materials, or acts, or to their equivalents.

The scope of protection is limited solely by the claims that now follow. That scope is intended and should be interpreted to be as broad as is consistent with the ordinary meaning of the language that is used in the claims when interpreted in light of this specification and the prosecution history that follows, except where specific meanings have been set forth, and to encompass all structural and functional equivalents.

Relational terms such as "first" and "second" and the like may be used solely to distinguish one entity or action from another, without necessarily requiring or implying any actual relationship or order between them. The terms "comprises," "comprising," and any other variation thereof when used in connection with a list of elements in the specification or claims are intended to indicate that the list is not exclusive and that other elements may be included. Similarly, an element preceded by an "a" or an "an" does not, without further constraints, preclude the existence of additional elements of the identical type.

None of the claims are intended to embrace subject matter that fails to satisfy the requirement of Sections 101, 102, or 103 of the Patent Act, nor should they be interpreted in such a way. Any unintended coverage of such subject matter is hereby disclaimed. Except as just stated in this paragraph, nothing that has been stated or illustrated is intended or should be interpreted to cause a dedication of any component, step, feature, object, benefit, advantage, or equivalent to the public, regardless of whether it is or is not recited in the claims.

The abstract is provided to help the reader quickly ascertain the nature of the technical disclosure. It is submitted with the understanding that it will not be used to interpret or limit the scope or meaning of the claims. In addition, various features in the foregoing detailed description are grouped together in various embodiments to streamline the disclosure. This method of disclosure should not be interpreted as requiring claimed embodiments to require more features than are expressly recited in each claim. Rather, as the following claims reflect, inventive subject matter lies in less than all features of a single disclosed embodiment. Thus, the following claims are hereby incorporated into the detailed description, with each claim standing on its own as separately claimed subject matter.

What is claimed is:

1. An apparatus for determining a composition of a metal artifact, the apparatus comprising:
   an electrical current source;
   the metal artifact to be tested;
   a first electrical cable and a second electrical cable different from the first electrical cable,
   wherein each of the first electrical cable and the second electrical cable is connected between the electrical current source and the metal artifact,
   wherein, during a test, the electrical current source outputs a current, and
   wherein, when the electrical current source outputs the current, the current travels through at least a portion of the metal artifact;
   a magnetic field sensor that detects, during the test, a magnetic field generated by the metal artifact when the current travels through the at least the portion of the metal artifact,
   wherein the magnetic field sensor is disposed within a predetermined distance of the metal artifact during the test; and
   a metal artifact holder that holds the metal artifact in a fixed position during the test,
   wherein the metal artifact holder does not include any ferrous material.

2. The apparatus of claim 1, wherein the electrical current source generates current at multiple different selectable levels.

3. The apparatus of claim 1, wherein the magnetic field sensor measures an intensity of the magnetic field and a direction of the magnetic field.

4. The apparatus of claim 3, wherein the magnetic field sensor is part of a mobile device.

5. The apparatus of claim 1, further comprising a sensor holder that detachably holds the magnetic field sensor in a fixed position during the test, wherein the sensor holder does not include any ferrous material.

6. The apparatus of claim 5, wherein the sensor holder is disposed with respect to the metal artifact holder so that the magnetic field sensor on the sensor holder is disposed within the predetermined distance of the metal artifact on the metal artifact holder during the test.

7. A method for determining a composition of a metal artifact, the method comprising:
   electrically connecting an electrical current source to the metal artifact so as to cause a current from the electrical current source to travel through at least a portion of the metal artifact;
   placing a magnetic field sensor within a predetermined distance of the metal artifact;
   activating the electrical current source to generate and output the current so that the current travels through the at least the portion of the metal artifact;
   measuring, using the magnetic field sensor, a magnetic field generated by the metal artifact while the current travels through the at least the portion of the metal artifact; and
   determining the composition of the metal artifact based on the measured magnetic field,
   wherein determining the composition of the metal artifact includes comparing the measured magnetic field to a magnetic field of a specific metal artifact having a predetermined composition.

8. The method of claim 7, further comprising:
   measuring earth's magnetic field with the magnetic field sensor before the metal artifact is within a predetermined distance of the magnetic field sensor,
   wherein the measured earth's magnetic field is used for determining as part of determining the composition of the metal artifact.

9. The method of claim 7, further comprising:
   measuring earth's magnetic field with the magnetic field sensor 1) while the metal artifact is within a predetermined distance of the magnetic field sensor and 2) before the current from the electrical current source is applied to the metal artifact,
   wherein the measured earth's magnetic field is used for determining the composition of the metal artifact.

10. The method of claim 7, further comprising:
    causing the current at different levels to travel through the at least the portion of the metal artifact;
    measuring, at each of the different levels, the magnetic field generated by the metal artifact while the current travels through the at least the portion of the metal artifact; and
    determining the composition of the metal artifact based on all of the measured magnetic fields of the at least the portion of the metal artifact.

11. The method of claim 7, wherein the predetermined composition includes a metal composition in the specific metal artifact.

12. The method of claim 10, further comprising adjusting a position to which the current is applied to from the at least the portion of the metal artifact to another portion of the metal artifact.

13. The method of claim 12, further comprising:
    causing the current at the different levels to travel through the another portion of the metal artifact;
    measuring, at each of the different levels, the magnetic field generated by the metal artifact while the current travels through the another portion of the metal artifact;
    determining the composition of the metal artifact based on all of the measured magnetic fields of the another portion of the metal artifact; and
    generating an electromagnetic profile based on the all of the measured magnetic fields of the at least the portion of the metal artifact and the all of the measured magnetic fields of the another portion of the metal artifact.

14. A method for determining a composition of a metal artifact, the method comprising:
    electrically connecting an electrical current source to the metal artifact so as to cause a current from the electrical current source to travel through at least a portion of the metal artifact;
    placing a magnetic field sensor within a predetermined distance of the metal artifact;
    activating the electrical current source to generate and output the current so that the current travels through the at least the portion of the metal artifact;
    measuring, using the magnetic field sensor, a magnetic field generated by the metal artifact while the current travels through the at least the portion of the metal artifact;

determining the composition of the metal artifact based on the measured magnetic field; and measuring earth's magnetic field with the magnetic field sensor before the metal artifact is within a predetermined distance of the magnetic field sensor, wherein the measured earth's magnetic field is used for determining as part of determining the composition of the metal artifact.

\* \* \* \* \*